(12) United States Patent
Scheller et al.

(10) Patent No.: US 9,149,389 B2
(45) Date of Patent: *Oct. 6, 2015

(54) MICROSURGICAL HANDLE AND INSTRUMENT

(75) Inventors: Gregg D Scheller, Wildwood, MO (US); Craig Moore, O'Fallon, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 364 days.

This patent is subject to a terminal disclaimer.

(21) Appl. No.: 13/602,045

(22) Filed: Aug. 31, 2012

(65) Prior Publication Data

US 2014/0066977 A1   Mar. 6, 2014

(51) Int. Cl.
*A61B 17/28* (2006.01)
*A61F 9/007* (2006.01)
*A61B 17/30* (2006.01)
*A61B 17/29* (2006.01)

(52) U.S. Cl.
CPC ............ *A61F 9/00754* (2013.01); *A61B 17/30* (2013.01); *A61B 17/2909* (2013.01); *A61B 2017/2918* (2013.01); *A61B 2017/2924* (2013.01); *A61B 2017/305* (2013.01)

(58) Field of Classification Search
CPC ............... A61B 17/28; A61B 17/2841; A61B 2017/2845; A61B 2017/2901; A61B 2017/2902; A61B 17/29; A61B 17/30; A61B 17/2909; A61B 2017/291; A61B 2017/2912; A61B 2017/2918

USPC ......... 606/205–207, 170, 171, 139, 182, 265, 606/13, 51, 52, 210
See application file for complete search history.

(56) References Cited

U.S. PATENT DOCUMENTS

| | | | |
|---|---|---|---|
| 5,355,871 A | 10/1994 | Hurley et al. | |
| 6,488,695 B1* | 12/2002 | Hickingbotham | 606/206 |
| 6,730,076 B2 | 5/2004 | Hickingbotham | |
| 6,863,668 B2 | 3/2005 | Gillespie et al. | |
| 7,632,242 B2 | 12/2009 | Griffin et al. | |
| 7,766,904 B2 | 8/2010 | McGowan, Sr. et al. | |
| 8,038,692 B2 | 10/2011 | Valencia et al. | |
| 8,197,468 B2 | 6/2012 | Scheller et al. | |
| 2003/0009854 A1* | 1/2003 | Shippert | 16/430 |
| 2003/0171762 A1 | 9/2003 | Forchette et al. | |
| 2005/0154403 A1* | 7/2005 | Sauer et al. | 606/139 |
| 2007/0185514 A1 | 8/2007 | Kirchhevel | |
| 2008/0287732 A1* | 11/2008 | Kuntz | 600/37 |
| 2012/0330286 A1* | 12/2012 | Seibold et al. | 606/1 |

* cited by examiner

*Primary Examiner* — Jonathan W Miles
*Assistant Examiner* — George J Ulsh
(74) *Attorney, Agent, or Firm* — Kevin P. Rollins (57) ABSTRACT

A microsurgical handle and instrument may include an actuation structure having an actuation structure distal end and an actuation structure proximal end, a plurality of actuation arms of the actuation structure, and an actuation structure base. A compression of the actuation structure may be configured to extend the actuation structure distal end relative to the actuation structure proximal end. A compression of the actuation structure may be configured to expand an extension joint of an actuation arm of the plurality of the actuation arms. A decompression of the actuation structure may be configured to retract the actuation structure distal end relative to the actuation structure proximal end. A decompression of the actuation structure may be configured to collapse an extension joint of an actuation arm of the plurality of actuation arms.

18 Claims, 7 Drawing Sheets

MICROSURGICAL HANDLE AND INSTRUMENT

FIELD OF THE INVENTION

The present disclosure relates to a medical device, and, more particularly, to a surgical instrument.

BACKGROUND OF THE INVENTION

A variety of surgical procedures are performed through a very small surgical incision in a particular tissue. Reducing the size of a surgical incision during a surgical procedure generally reduces the amount of trauma to the surgical site and generally facilitates faster wound healing. In order to perform surgical procedures through a very small surgical incision, a surgeon may require specialized surgical instruments configured to fit through the very small surgical incision and provide the surgeon with a surgical utility. Sometimes a surgeon may require a surgical utility that may not be easily controlled close to a particular surgical site, e.g., closing forceps jaws inside of an eye. It is generally desirable for a surgeon to be able to control such a surgical utility with a minimal amount of effort. For example, if a surgical utility is controlled by a lever or a switch on an instrument handle, a surgeon may need to adjust an orientation of a surgical instrument in order to actuate the lever or the switch. Additionally, if a surgical utility control requires a surgeon to apply a significant amount of force to a portion of a surgical instrument, then it may be difficult for the surgeon to manipulate the surgical utility control without unintentionally moving a portion of the surgical instrument.

However, it is important that some effort is required to manipulate a surgical utility control of a surgical instrument. For example, if manipulation of a surgical utility control only requires a surgeon to apply a very small force to a portion of a surgical instrument, then it may be possible for the surgeon to unintentionally manipulate a surgical utility control during a surgical procedure. Accordingly, there is a need for a surgical instrument handle to control a surgical utility through a very small surgical incision with an optimal amount of effort.

BRIEF SUMMARY OF THE INVENTION

The present disclosure presents a microsurgical handle and instrument. Illustratively, a microsurgical handle and instrument may comprise an actuation structure having an actuation structure distal end and an actuation structure proximal end, a plurality of actuation arms of the actuation structure, and an actuation structure base. In one or more embodiments, a compression of the actuation structure may be configured to extend the actuation structure distal end relative to the actuation structure proximal end. Illustratively, a compression of the actuation structure may be configured to expand an extension joint of an actuation arm of the plurality of the actuation arms. In one or more embodiments, a decompression of the actuation structure may be configured to retract the actuation structure distal end relative to the actuation structure proximal end. Illustratively, a decompression of the actuation structure may be configured to collapse an extension joint of an actuation arm of the plurality of actuation arms.

BRIEF DESCRIPTION OF THE DRAWINGS

The above and further advantages of the present invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1A:
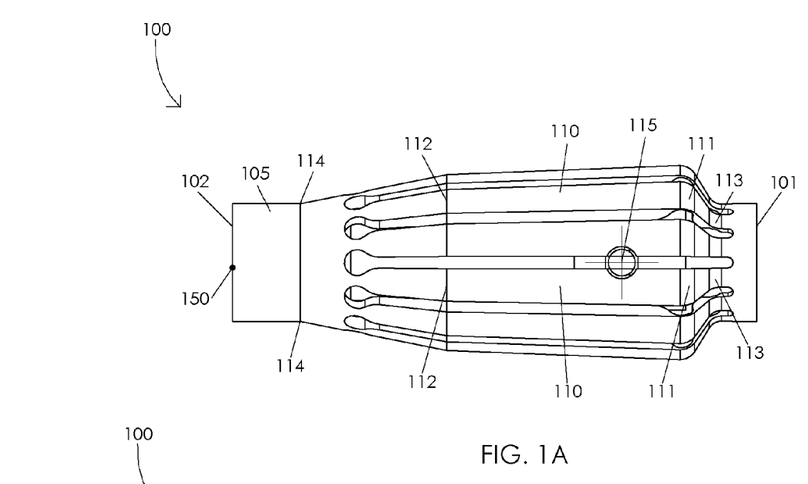
FIGS. 1A, 1B, 1C, 1D, 1E, 1F, 1G, and 1H are schematic diagrams illustrating an actuation structure.

FIGS. 1A, 1B, 1C, 1D, 1E, 1F, 1G, and 1H are schematic diagrams illustrating an actuation structure 100. FIG. 1A illustrates a top view of a decompressed actuation structure 100. Illustratively, actuation structure 100 may comprise an actuation structure distal end 101 and an actuation structure proximal end 102, an actuation structure base 105, a plurality of actuation arms 110, an actuation structure base interface 114, and a fixation mechanism housing 115. In one or more embodiments, each actuation arm 110 of a plurality of actuation arms 110 may comprise an extension joint 111, a distal extension mechanism 113, and a proximal extension mechanism 112. Illustratively, actuation structure distal end 101 may extend a decompressed distance from actuation structure proximal end 102, e.g., when actuation structure 100 comprises a decompressed actuation structure 100. In one or more embodiments, a decompressed distance may be between 1.6 and 3.0 inches, e.g., a decompressed distance may be 2.25 inches. Illustratively, a decompressed distance may be less than 1.6 inches or greater than 3.0 inches.

Figure 1B:
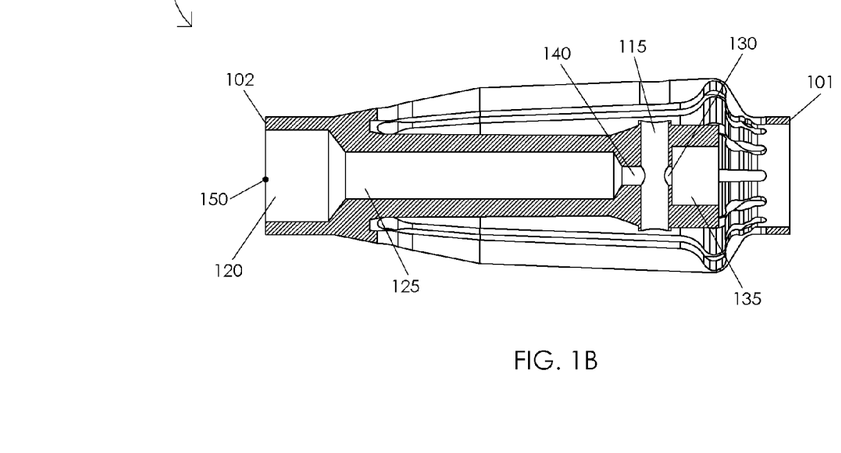
Figure 1C:
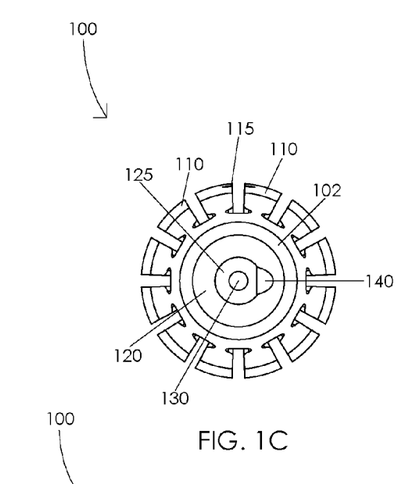
Figure 1D:
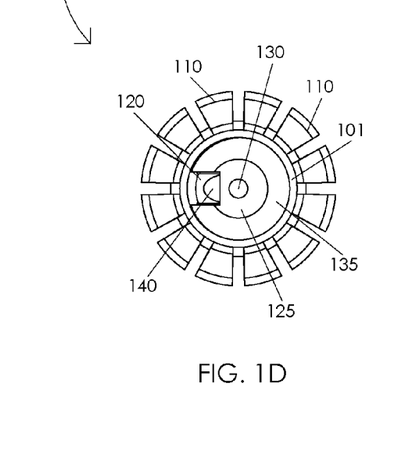

FIG. 1B illustrates a cross-sectional view of a decompressed actuation structure 100. Illustratively, actuation structure 100 may comprise a handle base housing 120, an inner bore 125, a capsulorhexis forceps shaft housing 130, an inner chamber 135, and an offset inner chamber 140. FIG. 1C illustrates a rear view of a decompressed actuation structure 100. FIG. 1D illustrates a front view of a decompressed actuation structure 100. In one or more embodiments, actuation structure 100 may be manufactured from any suitable material, e.g., polymers, metals, metal alloys, etc., or from any combination of suitable materials. Illustratively, actuation structure 100 may be manufactured from a shape memory material. In one or more embodiments, actuation structure 100 may be manufactured using a selective laser sintering machine. Illustratively, actuation structure 100 may be manufactured by additive manufacturing or 3D printing.

In one or more embodiments, actuation structure 100 may have a density between 0.02 and 0.05 pounds per cubic inch, e.g., actuation structure 100 may have a density of 0.036 pounds per cubic inch. Illustratively, actuation structure 100 may have a density less than 0.02 pounds per cubic inch or greater than 0.05 pounds per cubic inch. In one or more embodiments, actuation structure 100 may have a mass between 0.005 and 0.025 pounds, e.g., actuation structure 100 may have a mass of 0.013 pounds. Illustratively, actuation structure 100 may have a mass less than 0.005 pounds or greater than 0.025 pounds. In one or more embodiments, actuation structure 100 may have a volume between 0.2 and 0.5 cubic inches, e.g., actuation structure 100 may have a volume of 0.365 cubic inches. Illustratively, actuation structure 100 may have a volume less than 0.2 cubic inches or greater than 0.5 cubic inches. In one or more embodiments, actuation structure 100 may have a surface area between 10.0 and 15.0 square inches, e.g., actuation structure 100 may have a surface area of 13.25 square inches. Illustratively, actuation structure 100 may have a surface area less than 10.0 square inches or greater than 15.0 square inches. With respect to reference origin 150, actuation structure 100 may have a center of mass at X=1.15 inches, Y=−0.00083 inches, and Z=−0.0086 inches.

In one or more embodiments, actuation structure 100 may be manufactured from a material suitable for sterilization by a medical autoclave. Illustratively, actuation structure 100 may be manufactured from a material, e.g., Nylon, configured to withstand exposure to temperatures, pressures, and ambient conditions present in a medical autoclave without degradation. For example, actuation structure 100 may be configured to function normally after exposure in a temperature 250° F. for 15 minutes at an atmospheric pressure of 15 psi. In one or more embodiments, actuation structure 100 may be configured to be used in a surgical procedure and then sterilized by a medical autoclave at least three times. Illustratively, actuation structure 100 may be configured to be used in a surgical procedure and then sterilized by a medical autoclave more than three times.

Figures 1E, 1F:
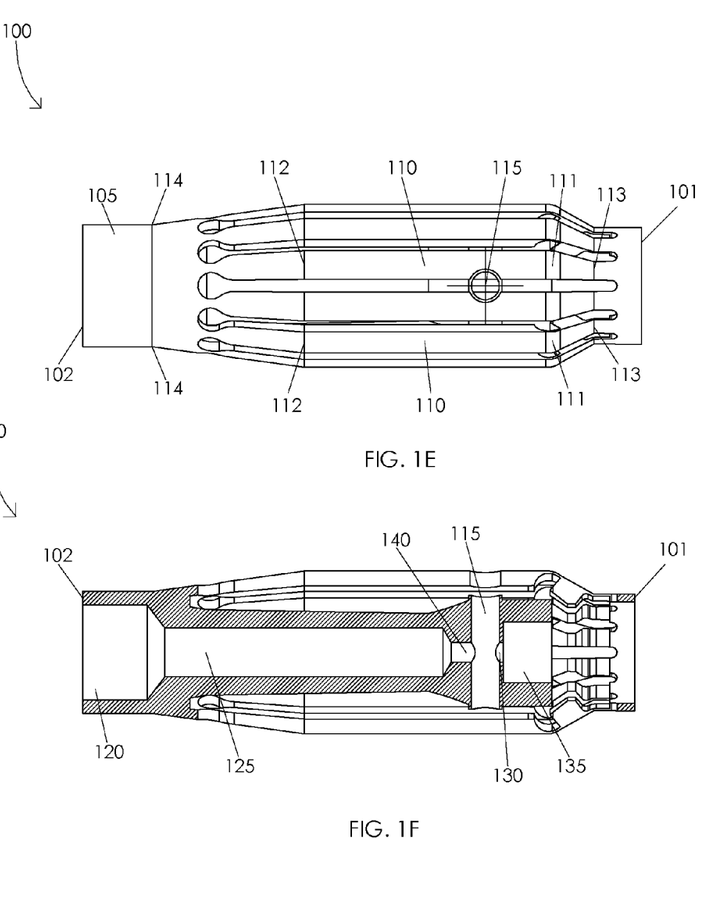
Figure 1G:
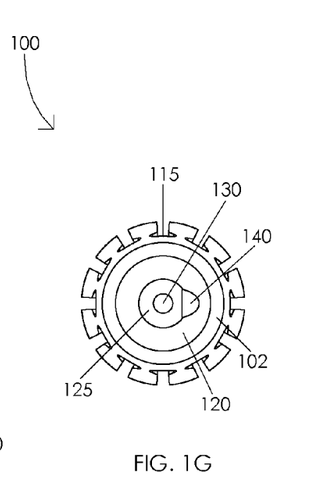
Figure 1H:
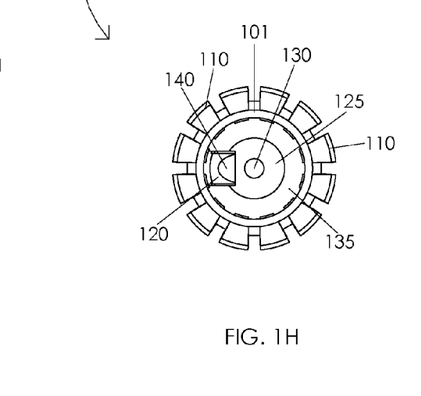

FIG. 1E illustrates a top view of a compressed actuation structure 100. FIG. 1F illustrates a cross-sectional view of a compressed actuation structure 100. FIG. 1G illustrates a rear view of a compressed actuation structure 100. FIG. 1H illustrates a front view of a compressed actuation structure 100. In one or more embodiments, actuation structure 100 may be configured to project actuation structure distal end 101 a first distance from actuation structure proximal end 102, e.g., when actuation structure 100 is fully decompressed. Illustratively, actuation structure 100 may comprise a shape memory material configured to project actuation structure distal end 101 a second distance from actuation structure proximal end 102, e.g., when actuation structure 100 is fully compressed. In one or more embodiments, the second distance from actuation structure proximal end 102 may be greater than the first distance from actuation structure proximal end 102. Illustratively, a compression of actuation structure 100 may be configured to gradually extend actuation structure distal end 101 relative to actuation structure proximal end 102.

In one or more embodiments, actuation structure distal end 101 may extend a compressed distance from actuation structure proximal end 102, e.g., when actuation structure 100 comprises a compressed actuation structure 100. Illustratively, a compressed distance may be between 1.6 and 3.0 inches, e.g., a compressed distance may be 2.26 inches. In one or more embodiments, a compressed distance may be less than 1.6 inches or greater than 3.0 inches. Illustratively, a compressed distance may be between 0.005 and 0.05 inches greater than a decompressed distance. In one or more embodiments, a compressed distance may be less than 0.005 inches greater than a decompressed distance. Illustratively, a compressed distance may be greater than 0.05 inches greater than a decompressed distance. In one or more embodiments, a compressed distance may be between 0.25 and 1.0 percent greater than a decompressed distance. Illustratively, a compressed distance may be less than 0.25 percent greater than a decompressed distance. In one or more embodiments, a compressed distance may be more than 1.0 percent greater than a decompressed distance.

Illustratively, actuation structure 100 may be compressed by an application of a force, e.g., a compressive force, to a portion of actuation structure 100. In one or more embodiments, an application of a compressive force of between 0.2 and 1.0 pounds may compress actuation structure 100, e.g., an application of a compressive force of 0.84 pounds may be configured to compress actuation structure 100. Illustratively, an application of a compressive force of less than 0.2 pounds or greater than 1.0 pounds may be configured to compress actuation structure 100. In one or more embodiments, actuation structure 100 may be compressed by an application of one or more compressive forces at one or more locations around an outer perimeter of actuation structure 100. Illustratively, the one or more locations may comprise any particular locations of a plurality of locations around an outer perimeter of actuation structure 100. For example, a surgeon may compress actuation structure 100 by squeezing actuation structure 100. Illustratively, a surgeon may compress actuation structure 100 by squeezing actuation structure 100 at any particular location of a plurality of locations around an outer perimeter of actuation structure 100.

In one or more embodiments, a surgeon may compress actuation structure 100 by applying a force to a portion of actuation structure 100, e.g., when actuation structure 100 is in a first rotational orientation. Illustratively, the surgeon may then rotate actuation structure 100 and compress actuation structure 100 by applying a force to a portion of actuation structure 100, e.g., when actuation structure 100 is in a second rotational orientation. In one or more embodiments, the surgeon may then rotate actuation structure 100 and compress actuation structure 100 by applying a force to a portion of actuation structure 100, e.g., when actuation structure 100 is in a third rotational orientation. Illustratively, a surgeon may compress actuation structure 100 by applying a force to a portion of actuation structure 100, e.g., when actuation structure 100 is in any rotational orientation.

In one or more embodiments, actuation structure 100 may be compressed by an application of a compressive force to any one or more actuation arms 110 of a plurality of actuation arms 110. Illustratively, each actuation arm 110 may be connected to one or more actuation arms 110 of a plurality of actuation arms 110 wherein an actuation of a particular actuation arm 110 may be configured to actuate every actuation arm 110 of a plurality of actuation arms 110. In one or more embodiments, one or more actuation arms 110 may be configured to actuate in pairs or groups. For example, an actuation of a first actuation arm 110 may be configured to actuate a second actuation arm 110.

Illustratively, a compression of actuation structure 100, e.g., due to an application of a force to a portion of actuation structure 100, may be configured to expand one or more extension joints 111 of a particular actuation arm 110. In one or more embodiments, an expansion of an extension joint 111 of a particular actuation arm 110 may be configured to increase a distance between a distal end and a proximal end of the particular actuation arm 110. Illustratively, an expansion of an extension joint 111 of a particular actuation arm 110 may be configured to expand an extension joint 111 of every actuation arm 110 of a plurality of actuation arms 110. In one or more embodiments, an expansion of an extension joint 111 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to collapse one or more extension joints 111 of a particular actuation arm 110. In one or more embodiments, a collapse of an extension joint 111 of a particular actuation arm 110 may be configured to decrease a distance between a distal end and a proximal end of the particular actuation arm 110. Illustratively, a collapse of an extension joint 111 of a particular actuation arm 110 may be configured to collapse an extension joint 111 of every actuation arm 110 of a plurality of actuation arms 110. In one or more embodiments, a collapse of an extension joint 111 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend a proximal extension mechanism 112 of a particular actuation arm 110. In one or more embodiments, an extension of a proximal extension mechanism 112 of a particular actuation arm 110 may be configured to increase a distance between a distal end and a proximal end of the particular actuation arm 110. Illustratively, an extension of a proximal extension mechanism 112 of a particular actuation arm 110 may be configured to extend a proximal extension mechanism 112 of every actuation arm 110 of a plurality of actuation arms 110. In one or more embodiments, an extension of a proximal extension mechanism 112 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract a proximal extension mechanism 112 of a particular actuation arm 110. In one or more embodiments, a retraction of a proximal extension mechanism 112 of a particular actuation arm 110 may be configured to decrease a distance between a distal end and a proximal end of the particular actuation arm 110. Illustratively, a retraction of a proximal extension mechanism 112 of a particular actuation arm 110 may be configured to retract a proximal extension mechanism 112 of every actuation arm 110 of a plurality of actuation arms 110. In one or more embodiments, a retraction of a proximal extension mechanism 112 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend a distal extension mechanism 113 of a particular actuation arm 110. In one or more embodiments, an extension of a distal extension mechanism 113 of a particular actuation arm 110 may be configured to increase a distance between a distal end and a proximal end of the particular actuation arm 110. Illustratively, an extension of a distal extension mechanism 113 of a particular actuation arm 110 may be configured to extend a distal extension mechanism 113 of every actuation arm 110 of a plurality of actuation arms 110. In one or more embodiments, an extension of a distal extension mechanism 113 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract a distal extension mechanism 113 of a particular actuation arm 110. In one or more embodiments, a retraction of a distal extension mechanism 113 of a particular actuation arm 110 may be configured to decrease a distance between a distal end and a proximal end of the particular actuation arm 110. Illustratively, a retraction of a distal extension mechanism 113 of a particular actuation arm 110 may be configured to retract a distal extension mechanism 113 of every actuation arm 110 of a plurality of actuation arms 110. In one or more embodiments, a retraction of a distal extension mechanism 113 of every actuation arm 110 of a plurality of actuation arms 110 may be configured to decrease a distance between actuation structure distal end 101 and actuation structure proximal end 102.

Illustratively, a compression of actuation structure 100, e.g., due to an application of a force to a portion of actuation structure 100, may be configured to extend an extension joint 111, a proximal extension mechanism 112, and a distal extension mechanism 113 of a particular actuation arm 110. In one or more embodiments, an extension of an extension joint 111, a proximal extension mechanism 112, and a distal extension mechanism 113 of a particular actuation arm 110 may be configured to increase a distance between a distal end and a proximal end of the particular actuation arm 110. Illustratively, an extension of an extension joint 111, a proximal extension mechanism 112, and a distal extension mechanism 113 of a particular actuation arm 110 may be configured to extend an extension joint 111, a proximal extension mechanism 112, and a distal extension mechanism 113 of every actuation arm 110 of a plurality of actuation arms 110. In one or more embodiments, an extension of an extension joint 111, a proximal extension mechanism 112, and a distal extension mechanism 113 of every actuation arm 110 of a plurality of actuation arms 110 may be configured to increase a distance between actuation structure distal end 101 and actuation structure proximal end 102.

Illustratively, a decompression of actuation structure 100, e.g., due to a reduction of a force applied to a portion of actuation structure 100, may be configured to retract an extension joint 111, a proximal extension mechanism 112, and a distal extension mechanism 113 of a particular actuation arm 110. In one or more embodiments, a refraction of an extension joint 111, a proximal extension mechanism 112, and a distal extension mechanism 113 of a particular actuation arm 110 may be configured to decrease a distance between a distal end and a proximal end of the particular actuation arm 110. Illustratively, a retraction of an extension joint 111, a proximal extension mechanism 112, and a distal extension mechanism 113 of a particular actuation arm 110 may be configured to retract an extension joint 111, a proximal extension mechanism 112, and a distal extension mechanism 113 of every actuation arm 110 of a plurality of actuation arms 110. In one or more embodiments, a retraction of an extension joint 111, a proximal extension mechanism 112, and a distal extension mechanism 113 of every actuation arm 110 of a plurality of actuation arms 110 may be configured to decrease a distance between actuation structure distal end 101 and actuation structure proximal end 102.

Figure 2A:
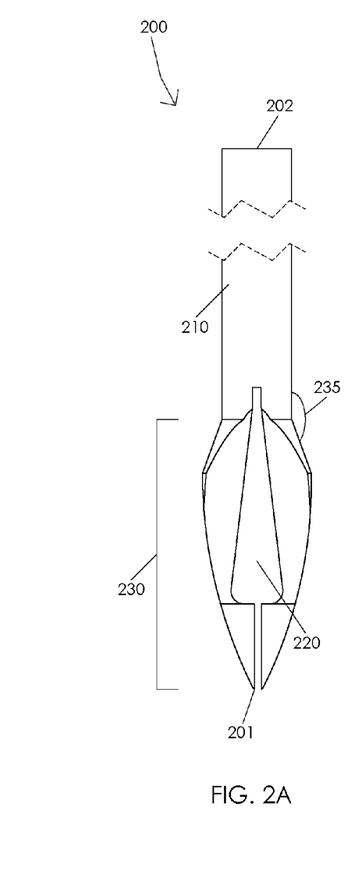
FIGS. 2A, 2B, 2C, 2D, 2E, 2F, 2G, and 2H are schematic diagrams illustrating a capsulorhexis forceps.
Figures 2B, 2C, 2D:
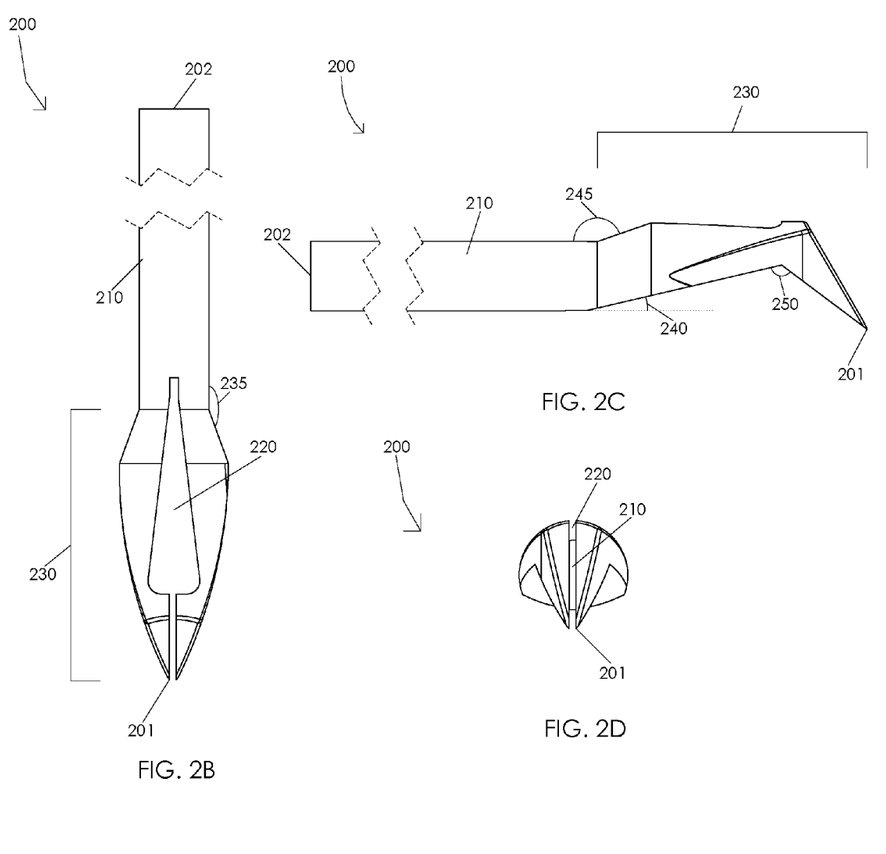

FIGS. 2A, 2B, 2C, 2D, 2E, 2F, 2G, and 2H are schematic diagrams illustrating a capsulorhexis forceps 200. FIG. 2A illustrates a bottom view of an open capsulorhexis forceps 200. Illustratively, capsulorhexis forceps 200 may comprise a capsulorhexis forceps distal end 201 and a capsulorhexis forceps proximal end 202. In one or more embodiments, capsulorhexis forceps 200 may comprise a capsulorhexis forceps shaft 210, a capsulorhexis forceps aperture 220, and capsulorhexis forceps jaws 230. FIG. 2B illustrates a top view of an open capsulorhexis forceps 200. Illustratively, capsulorhexis forceps jaws 230 may interface with capsulorhexis forceps shaft 210 at a capsulorhexis forceps shaft interface angle 235. In one or more embodiments, capsulorhexis forceps shaft interface angle 235 may comprise any angle greater than 90 degrees.

FIG. 2C illustrates a side view of an open capsulorhexis forceps 200. In one or more embodiments, capsulorhexis forceps 200 may be contoured at a first capsulorhexis forceps jaws angle 240, a second capsulorhexis forceps jaws angle 245, and a third capsulorhexis forceps jaws angle 250. Illustratively, first capsulorhexis forceps jaws angle 240 may comprise any angle less than 90 degrees. In one or more embodiments, second capsulorhexis forceps jaws angle 245 may comprise any angle greater than 90 degrees. Illustratively, third capsulorhexis forceps jaws angle 250 may comprise an angle between 120 degrees and 140 degrees, e.g., third capsulorhexis forceps jaws angle 250 may comprise a 131 degree angle. FIG. 2D illustrates a front view of an open capsulorhexis forceps 200.

Figure 2E:
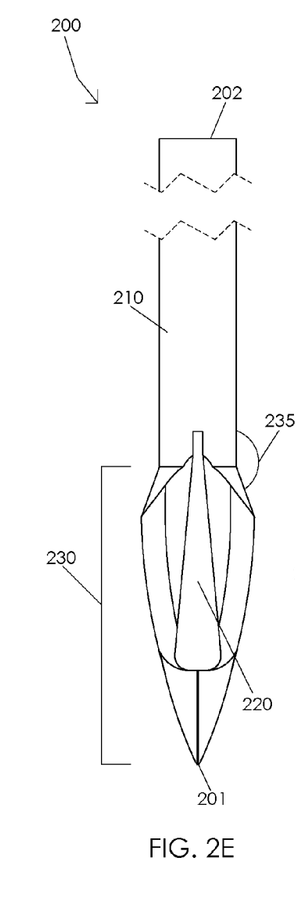
Figure 2F:
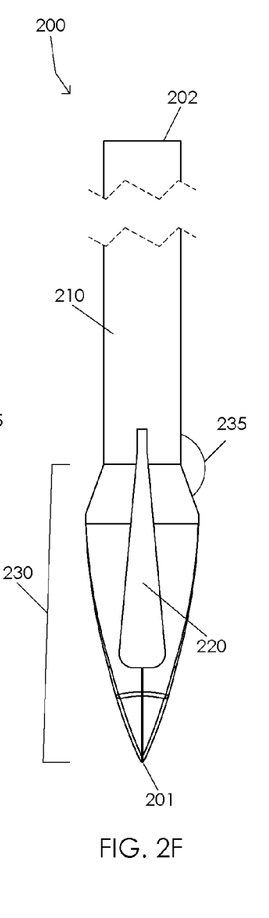
Figure 2G:
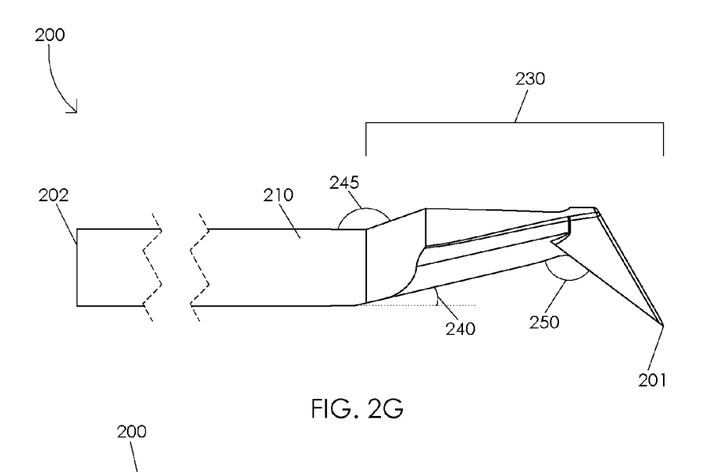
Figure 2H:
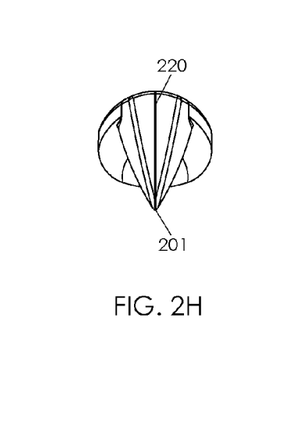

FIG. 2E illustrates a bottom view of a closed capsulorhexis forceps 200. FIG. 2F illustrates a top view of a closed capsulorhexis forceps 200. FIG. 2G illustrates a side view of a closed capsulorhexis forceps 200. FIG. 2H illustrates a front view of a closed capsulorhexis forceps 200. Illustratively, capsulorhexis forceps 200 may be manufactured from any suitable material, e.g., polymers, metals, metal alloys, etc., or from any combination of suitable materials. In one or more embodiments, capsulorhexis forceps 200 may be manufactured with dimensions suitable for performing microsurgical procedure, e.g., capsulorhexis forceps 200 may be manufactured with dimensions suitable for performing ophthalmic surgical procedures.

Figure 3:
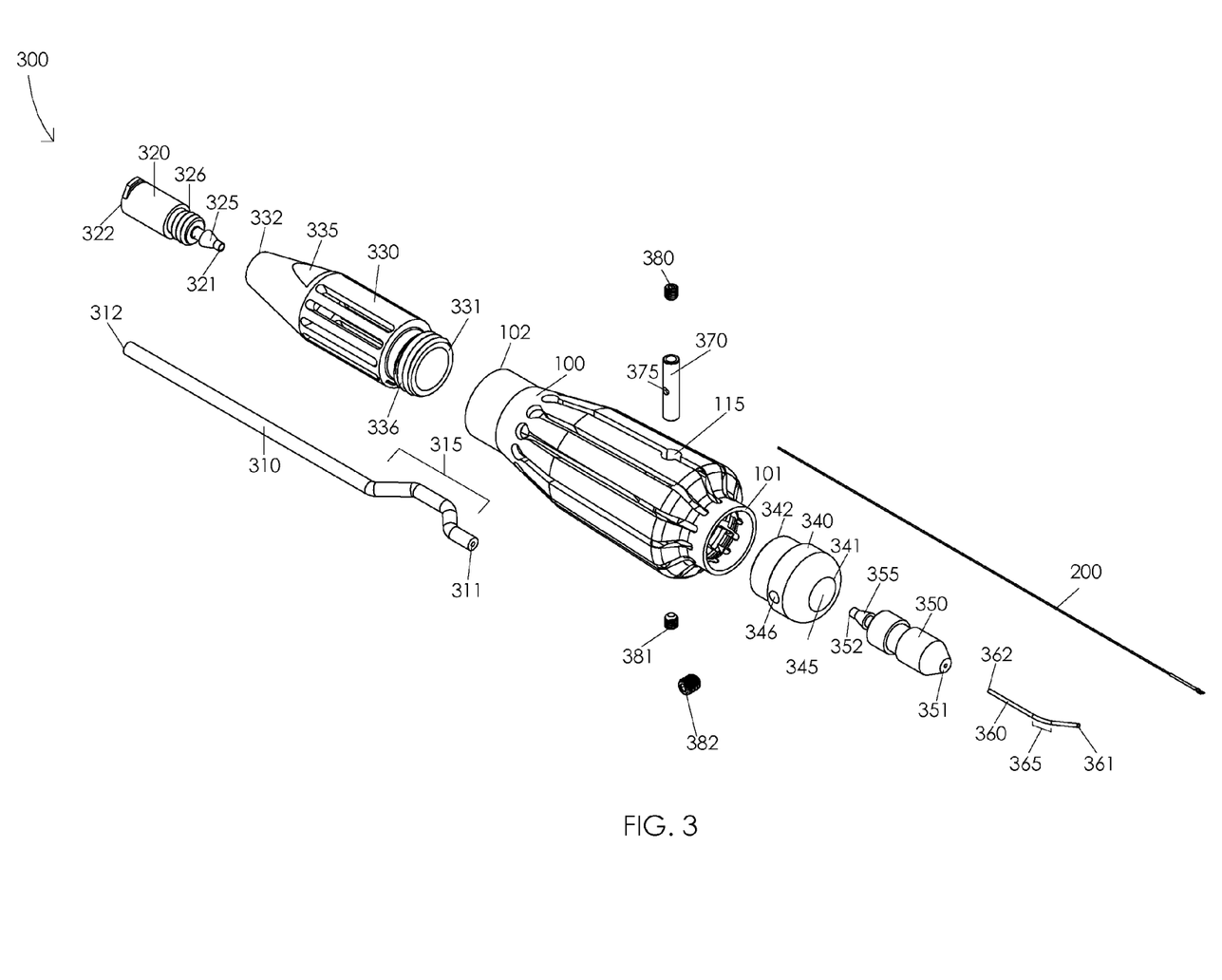
FIG. 3 is a schematic diagram illustrating an exploded view of a surgical instrument assembly.

FIG. 3 is a schematic diagram illustrating an exploded view of a surgical instrument assembly 300. Illustratively, a surgical instrument assembly may comprise a tube 310 having a tube distal end 311 and a tube proximal end 312, an end plug 320 having an end plug distal end 321 and an end plug proximal end 322, a handle base 330 having a handle base distal end 331 and a handle base proximal end 332, an actuation structure 100 having an actuation structure distal end 101 and an actuation structure proximal end 102, an outer nosecone 340 having an outer nosecone distal end 341 and an outer nosecone proximal end 342, an inner nosecone 350 having an inner nosecone distal end 351 an inner nosecone proximal end 352, an actuation sleeve 360 having an actuation sleeve distal end 361 and an actuation sleeve proximal end 362, a wire lock 370, a first fixation mechanism 380, a second fixation mechanism 381, and a nosecone fixation mechanism 382. In one or more embodiments, tube 310 may comprise a tube curved portion 315. Illustratively, tube curved portion 315 may be configured to curve tube 310 around wire lock 370.

In one or more embodiments, tube 310 may be manufactured from a material suitable for sterilization by a medical autoclave. Illustratively, tube 310 may be manufactured from a material configured to withstand exposure to temperatures, pressures, and ambient conditions present in a medical autoclave without degradation. For example, tube 310 may be configured to function normally after exposure in a temperature 250° F. for 15 minutes at an atmospheric pressure of 15 psi. In one or more embodiments, tube 310 may be configured to be used in a surgical procedure and then sterilized by a medical autoclave at least three times. Illustratively, tube 310 may be configured to be used in a surgical procedure and then sterilized by a medical autoclave more than three times.

In one or more embodiments, end plug 320 may comprise an end plug thread 326 and a proximal barb fitting 325. Illustratively, end plug 320 may comprise a lure hub. For example, end plug 320 may comprise an inner bore aligned with an inner bore of proximal barb fitting 325. In one or more embodiments, proximal barb fitting 325 may be configured to interface with tube proximal end 312. Illustratively, a portion of end plug 320 may be disposed within handle base 330, e.g., end plug distal end 321 may be disposed within handle base 330. In one or more embodiments, a portion of end plug 320 may be fixed within handle base 330, e.g., by an adhesive or any suitable fixation means. Illustratively, a portion of end plug 320 may be fixed within handle base 330, e.g., a portion of handle base 330 may comprise a thread configured to match end plug thread 326 and end plug 320 may be screwed into handle base 330. In one or more embodiments, a portion of end plug 320 may be fixed within handle base 330 by a press fit, a setscrew, etc. Illustratively, end plug 320 and handle base 330 may comprise a single unit. In one or more embodiments, end plug 320 may be manufactured from any suitable material, e.g., polymers, metals, metal alloys, etc., or from any combination of suitable materials.

In one or more embodiments, end plug 320 may be manufactured from a material suitable for sterilization by a medical autoclave. Illustratively, end plug 320 may be manufactured from a material configured to withstand exposure to temperatures, pressures, and ambient conditions present in a medical autoclave without degradation. For example, end plug 320 may be configured to function normally after exposure in a temperature 250° F. for 15 minutes at an atmospheric pressure of 15 psi. In one or more embodiments, end plug 320 may be configured to be used in a surgical procedure and then sterilized by a medical autoclave at least three times. Illustratively, end plug 320 may be configured to be used in a surgical procedure and then sterilized by a medical autoclave more than three times.

Illustratively, handle base 330 may comprise an assembly grip point 335 and a handle base thread 336. In one or more embodiments, a portion of handle base 330 may be disposed within actuation structure 100, e.g., handle base distal end 331 may be disposed within handle base housing 120. Illustratively, a portion of handle base 330 may be fixed within actuation structure 100, e.g., by an adhesive or any suitable fixation means. In one or more embodiments, a portion of handle base 330 may be fixed within a portion of actuation structure 100, e.g., a portion of actuation structure 100 may comprise a thread configured to match handle base thread 336 and handle base 330 may be screwed into actuation structure 100. Illustratively, assembly grip point 335 may be configured facilitate a fixation of a portion of handle base 330 within actuation structure 100, e.g., assembly grip point 335 may be configured to facilitate a screwing of handle base into actuation structure. In one or more embodiments, a portion of handle base 330 may be fixed within actuation structure 100 by a press fit, a setscrew, etc. Illustratively, handle base 330 and actuation structure 100 may comprise a single unit. For example, end plug 320, handle base 330, and actuation structure 100 may comprise a single unit. In one or more embodiments, handle base 330 may be manufactured from any suitable material, e.g., polymers, metals, metal alloys, etc., or from any combination of suitable materials.

In one or more embodiments, handle base 330 may be manufactured from a material suitable for sterilization by a medical autoclave. Illustratively, handle base 330 may be manufactured from a material configured to withstand exposure to temperatures, pressures, and ambient conditions present in a medical autoclave without degradation. For example, handle base 330 may be configured to function normally after exposure in a temperature 250° F. for 15 minutes at an atmospheric pressure of 15 psi. In one or more embodiments, handle base 330 may be configured to be used in a surgical procedure and then sterilized by a medical autoclave at least three times. Illustratively, handle base 330 may be configured to be used in a surgical procedure and then sterilized by a medical autoclave more than three times.

Illustratively, outer nosecone 340 may comprise an outer nosecone inner chamber 345 and a nosecone fixation mechanism housing 346. In one or more embodiments, inner nosecone 350 may comprise a distal barb fitting 355. For example, inner nosecone 350 may comprise an inner bore aligned with an inner bore of distal barb fitting 355. Illustratively, distal barb fitting 355 may be configured to interface with tube distal end 311. In one or more embodiments, a portion of inner nosecone 350 may be disposed within outer nosecone inner chamber 345, e.g., inner nosecone proximal end 352 may be disposed within outer nosecone inner chamber 345. Illustratively, inner nosecone 350 may be fixed within outer nosecone inner chamber 345, e.g., by an adhesive or any suitable fixation means. In one or more embodiments, nosecone fixation mechanism 382 may be configured to fix inner nosecone 350 to outer nosecone 340. Illustratively, nosecone fixation mechanism 382 may be disposed within nosecone fixation mechanism housing 346. In one or more embodiments, a portion of inner nosecone 350 may be fixed to a portion of nosecone fixation mechanism 382, e.g., by an adhesive or any suitable fixation means. Illustratively, nosecone fixation mechanism 382 may comprise a setscrew configured to fix inner nosecone 350 to outer nosecone 340, e.g., by a press fit or any suitable fixation means. In one or more embodiments, inner nosecone 350 and outer nosecone 340 may comprise a single unit. Illustratively, inner nosecone 350 and outer nosecone 340 may be manufactured from any suitable material, e.g., polymers, metals, metal alloys, etc., or from any combination of suitable materials.

In one or more embodiments, a portion of outer nosecone 340 may be fixed to actuation structure 100, e.g., outer nosecone proximal end 342 may be fixed to actuation structure distal end 101. Illustratively, a portion of outer nosecone 340 may be fixed to actuation structure 100, e.g., by an adhesive or any suitable fixation means. In one or more embodiments, a portion of outer nosecone 340 may be disposed within a portion of actuation structure 100, e.g., outer nosecone proximal end 342 may be disposed within a portion of actuation structure 100. Illustratively, a portion of outer nosecone 340 may be fixed within a portion of actuation structure 100, e.g., by an adhesive or any suitable fixation means.

In one or more embodiments, actuation sleeve 360 may comprise an actuation sleeve curved portion 365. Illustratively, actuation sleeve curved portion 365 may be configured to facilitate a performance of a capsulorhexis surgical procedure. In one or more embodiments, a portion of actuation sleeve 360 may be fixed to a portion of inner nosecone 350, e.g., actuation sleeve proximal end 362 may be fixed to inner nosecone distal end 351. Illustratively, a portion of actuation sleeve 360 may be fixed to a portion of inner nosecone 350, e.g., by an adhesive or any suitable fixation means. In one or more embodiments, a portion of actuation sleeve 360 may be disposed within a portion of inner nosecone 350, e.g., actuation sleeve proximal end 362 may be disposed within inner nosecone 350. Illustratively, a portion of actuation sleeve 360 may be fixed within inner nosecone 350, e.g., by an adhesive or any suitable fixation means. In one or more embodiments, a portion of actuation sleeve 360 may be fixed within inner nosecone 350, e.g., by a press fit, a setscrew, etc. Illustratively, actuation sleeve 360 may be manufactured from any suitable material, e.g., polymers, metals, metal alloys, etc., or from any combination of suitable materials.

In one or more embodiments, tube proximal end 312 may interface with proximal barb 325. Illustratively, a portion of tube 310 may be configured to fit over a portion of proximal barb 325, e.g., to form a hermetic seal. In one or more embodiments, tube 310 may be disposed within handle base 330, handle base housing 120, inner bore 125, offset inner chamber 140, inner chamber 135, and outer nosecone 340. Illustratively, tube 310 may be disposed with actuation structure 100 wherein tube curved portion 315 may be disposed in offset inner chamber 140. In one or more embodiments, tube distal end 311 may interface with distal barb 355. Illustratively, a portion of tube 310 may be configured to fit over a portion of distal barb 355, e.g., to form a hermetic seal.

In one or more embodiments, wire lock 370 may be disposed within fixation mechanism housing 115. Illustratively, wire lock 370 may be fixed within fixation mechanism housing 115, e.g., by an adhesive or any suitable fixation means. In one or more embodiments, capsulorhexis forceps 200 may be disposed within actuation structure 100 and actuation sleeve 360. Illustratively, capsulorhexis forceps shaft 210 may be disposed within wire lock 370, wire lock interface 375, capsulorhexis forceps shaft housing 130, inner chamber 135, outer nosecone 340, inner nosecone 350, and actuation sleeve 360. In one or more embodiments, a portion of capsulorhexis forceps 200 may extend from actuation sleeve distal end 361. Illustratively, at least a portion of capsulorhexis forceps jaws 230 may extend from actuation sleeve distal end 361. In one or more embodiments, capsulorhexis forceps shaft 210 may be fixed within wire lock 370, e.g., by an adhesive or any suitable fixation means. Illustratively, first fixation mechanism 380 and second fixation mechanism 381 may be configured to fix a portion of capsulorhexis forceps shaft 210 within wire lock 370, e.g., first fixation mechanism 380 and second fixation mechanism 381 may be disposed within wire lock 370. In one or more embodiments, first fixation mechanism 380 and second fixation mechanism 381 may comprise setscrews configured to firmly fix a portion of capsulorhexis forceps shaft 210 within wire lock 370.

Illustratively, a compression of actuation structure 100 may be configured to extend actuation structure distal end 101 relative to actuation structure proximal end 102, e.g., a compression of actuation structure 100 may be configured to increase a distance between actuation structure distal end 101 and actuation structure proximal end 102. In one or more embodiments, an extension of actuation structure distal end 101 relative to actuation structure proximal end 102 may be configured to extend outer nosecone 340 relative to handle base 330. Illustratively, an extension of outer nosecone 340 relative to handle base 330 may be configured to extend inner nosecone 350 relative to capsulorhexis forceps 200. In one or more embodiments, an extension of inner nosecone 350 relative to capsulorhexis forceps 200 may be configured to extend actuation sleeve 360 relative to capsulorhexis forceps jaws 230. Illustratively, a compression of actuation structure 100 may be configured to extend actuation sleeve 360 relative to capsulorhexis forceps jaws 230. In one or more embodiments, a compression of actuation structure 100 may be configured to extend actuation sleeve distal end 361 over a portion of capsulorhexis forceps jaws 230.

Illustratively, a decompression of actuation structure 100 may be configured to retract actuation structure distal end 101 relative to actuation structure proximal end 102, e.g., a decompression of actuation structure 100 may be configured to reduce a distance between actuation structure distal end 101 and actuation structure proximal end 102. In one or more embodiments, a refraction of actuation structure distal end 101 relative to actuation structure proximal end 102 may be configured to retract outer nosecone 340 relative to handle base 330. Illustratively, a retraction of outer nosecone 340 relative to handle base 330 may be configured to retract inner nosecone 350 relative to capsulorhexis forceps 200. In one or more embodiments, a refraction of inner nosecone 350 relative to capsulorhexis forceps 200 may be configured to retract actuation sleeve 360 relative to capsulorhexis forceps jaws 230. Illustratively, a decompression of actuation structure 100 may be configured to retract actuation sleeve 360 relative to capsulorhexis forceps jaws 230. In one or more embodiments, a decompression of actuation structure 100 may be configured to retract actuation sleeve distal end 361 away from a portion of capsulorhexis forceps jaws 230.

Figure 4A:
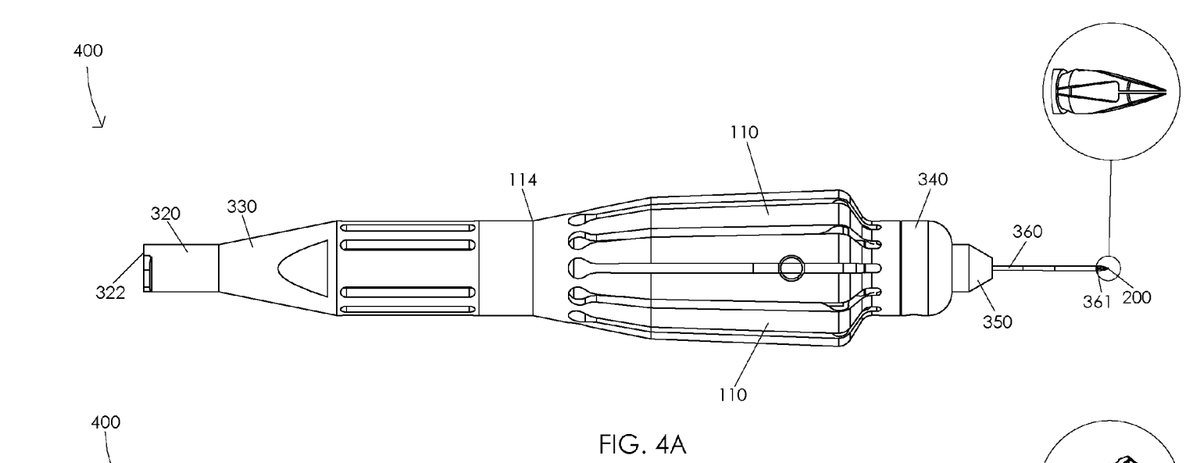
FIGS. 4A and 4B are schematic diagrams illustrating a retracted actuation sleeve.
Figure 4B:
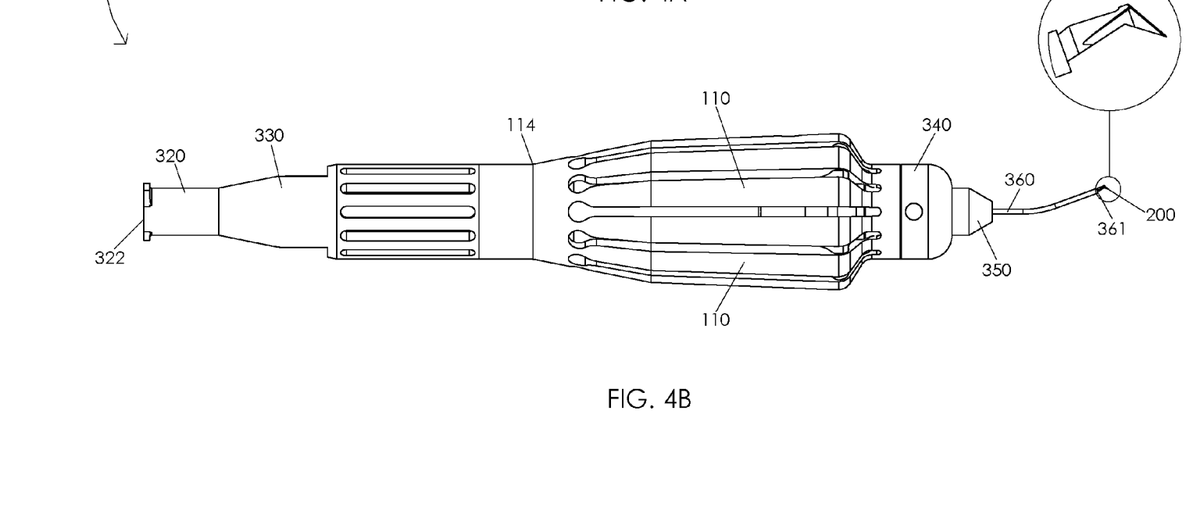

FIGS. 4A and 4B are schematic diagrams illustrating a retracted actuation sleeve 400. FIG. 4A illustrates a top view of a retracted actuation sleeve 400. In one or more embodiments, capsulorhexis forceps jaws 230 may comprise open capsulorhexis forceps jaws 230, e.g., when actuation sleeve 360 comprises a retracted actuation sleeve 400. FIG. 4B illustrates a side view of a retracted actuation sleeve 400. Illustratively, actuation sleeve 360 may comprise a retracted actuation sleeve 400, e.g., when actuation structure 100 is fully decompressed.

Figures 5A, 5B:
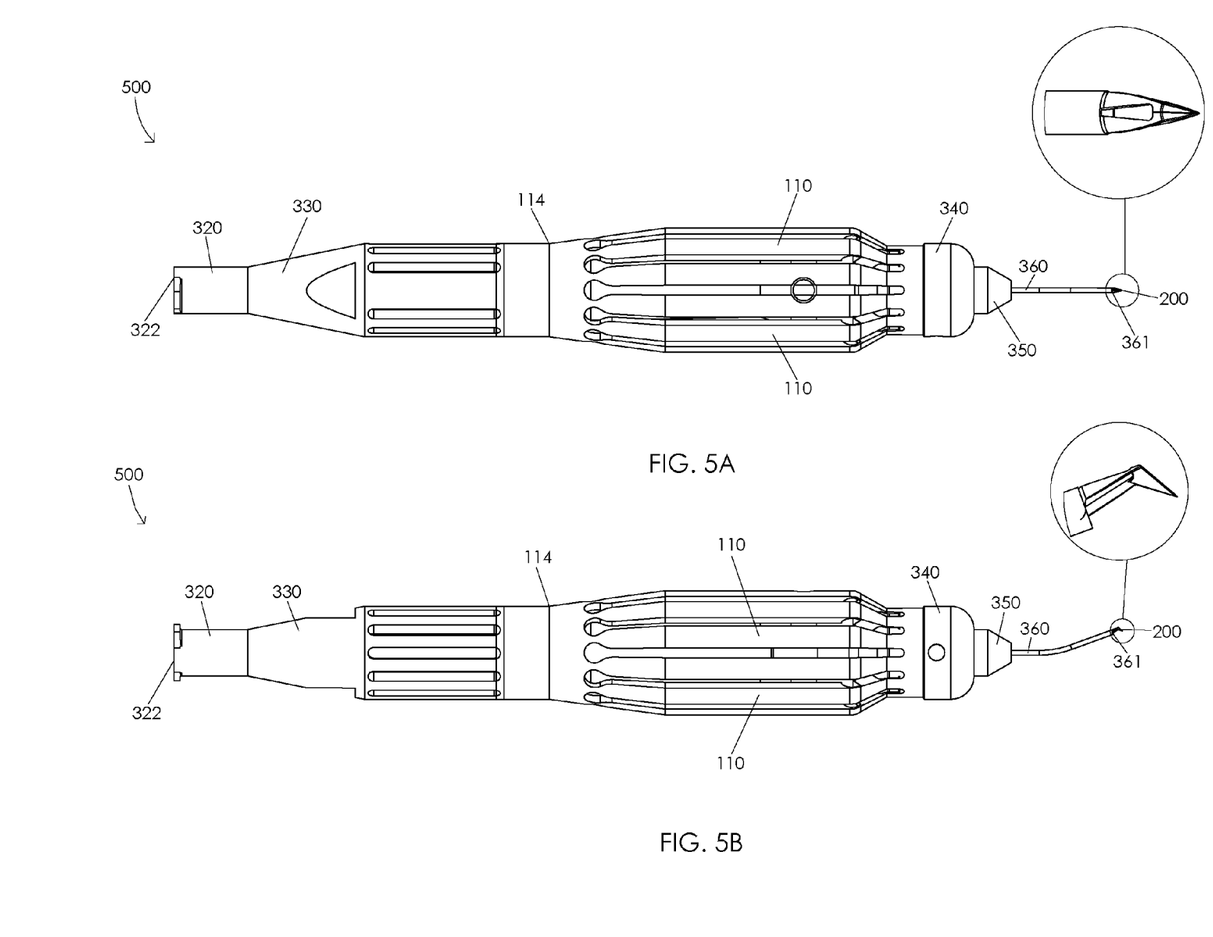
FIGS. 5A and 5B are schematic diagrams illustrating an extended actuation sleeve.

FIGS. 5A and 5B are schematic diagrams illustrating an extended actuation sleeve 500. FIG. 5A illustrates a top view of an extended actuation sleeve 500. Illustratively, capsulorhexis forceps jaws 230 may comprise closed capsulorhexis forceps jaws 230, e.g., when actuation sleeve 360 comprises an extended actuation sleeve 500. FIG. 5B illustrates a side view of an extended actuation sleeve 500. In one or more embodiments, actuation sleeve 360 may comprise an extended actuation sleeve 500, e.g., when actuation structure 100 is fully compressed.

Illustratively, a compression of actuation structure 100 may be configured to gradually extend actuation sleeve 360, e.g., from a retracted actuation sleeve 400 to an extended actuation sleeve 500. In one or more embodiments, an extension of actuation sleeve 360 relative to capsulorhexis forceps 200 may be configured to extend actuation sleeve 360 over a portion of capsulorhexis forceps jaws 230. Illustratively, an extension of actuation sleeve 360 over a portion of capsulorhexis forceps jaws 230 may be configured to gradually close capsulorhexis forceps jaws 230. In one or more embodiments, a compression of actuation structure 100 may be configured to gradually close capsulorhexis forceps jaws 230. For example, a surgeon may compress actuation structure 100 to grasp a tissue between capsulorhexis forceps jaws 230.

Illustratively, a decompression of actuation structure 100 may be configured to gradually retract actuation sleeve 360, e.g., from an extended actuation sleeve 500 to a refracted actuation sleeve 400. In one or more embodiments, a retraction of actuation sleeve 360 relative to forceps 200 may be configured to retract actuation sleeve 360 away from a portion of capsulorhexis forceps jaws 230. Illustratively, a retraction of actuation sleeve 360 away from a portion of capsulorhexis forceps jaws 230 may be configured to gradually open capsulorhexis forceps jaws 230. In one or more embodiments, a decompression of actuation structure 100 may be configured to gradually open capsulorhexis forceps jaws 230. For example, a surgeon may decompress actuation structure 100 to release a tissue from capsulorhexis forceps jaws 230.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to systems where the functionality may be employed. Therefore, it is the object of the appended claims to cover all such variations and modifications as come within the true spirit and scope of the invention.

What is claimed is:

1. An instrument handle comprising: an actuation structure having an actuation structure distal end and an actuation structure proximal end, the actuation structure manufactured from a polymer; a plurality of actuation arms of the actuation structure, each actuation arm of the plurality of actuation arms having an extension joint, a proximal extension mechanism, and a distal extension mechanism wherein the extension joint is disposed between the proximal extension mechanism and the distal extension mechanism; an inner bore of the actuation structure; a handle base housing of the actuation structure; a handle base having a handle base distal end and a handle base proximal end, an end plug fixed to the handle base; and a nosecone fixed to the actuation structure; and a tube curved portion of the tube, the tube curved portion disposed in the inner bore of the actuation structure wherein the tube proximal end is disposed over a proximal barb fitting of the end plug and the tube distal end is disposed over a distal barb fitting of the nosecone; the handle base distal end disposed within the handle base housing wherein the handle base is fixed to the actuation structure; an inner chamber of the actuation structure wherein the inner bore is disposed between the handle base housing and the inner chamber; a fixation mechanism housing of the actuation structure wherein the fixation mechanism housing is disposed between the inner chamber and the inner bore; a tube having a tube distal end and a tube proximal end, the tube disposed in the inner bore of the actuation structure and in the handle base; an actuation structure base of the actuation structure; and a surface area of the actuation structure, the surface area of the actuation structure in a range of 10.0 to 15.0 square inches wherein the actuation structure is configured to be used in a first surgical procedure and function normally after a first sterilization in a medical autoclave, used in a second surgical procedure and function normally after a second sterilization in the medical autoclave, and used in a third surgical procedure and function normally after a third sterilization in the medical autoclave.

2. The instrument handle of claim 1 wherein a compression of the actuation structure is configured to extend the actuation structure distal end relative to the actuation structure proximal end.

3. The instrument handle of claim 2 wherein the compression of the actuation structure is configured to expand the extension joint of each actuation arm of the plurality of actuation arms.

4. The instrument handle of claim 2 wherein the compression of the actuation structure is configured to extend the actuation structure distal end a distance in a range of 0.005 to 0.05 inches from the actuation structure proximal end.

5. The instrument handle of claim 2 wherein the compression of the actuation structure is configured to increase a distance between the actuation structure distal end and the actuation structure proximal end by a range of 0.25 to 1.0 percent.

6. The instrument handle of claim 1 wherein a decompression of the actuation structure is configured to retract the actuation structure distal end relative to the actuation structure proximal end.

7. The instrument handle of claim 6 wherein the decompression of the actuation structure is configured to collapse the extension joint of each actuation arm of the plurality of actuation arms.

8. The instrument handle of claim 1 wherein the actuation structure has a mass in a range of 0.005 to 0.025 pounds.

9. The instrument handle of claim 1 wherein the actuation structure has a density in a range of 0.02 to 0.05 pounds per cubic inch.

10. The instrument handle of claim 1 wherein the actuation structure has a volume in a range of 0.2 to 0.5 cubic inches.

11. The instrument handle of claim 1 wherein the actuation structure is manufactured by a selective laser sintering machine.

12. The instrument handle of claim 1 wherein the actuation structure is manufactured by a 3D printing machine.

13. The instrument handle of claim 1 further comprising: an actuation sleeve fixed to the nosecone; and a capsulorhexis forceps having a capsulorhexis forceps shaft and a capsulorhexis forceps jaws, the capsulorhexis forceps disposed in the actuation sleeve, the nosecone, and a capsulorhexis forceps shaft housing of the actuation structure.

14. The instrument handle of claim 13 wherein a compression of the actuation structure is configured to close the capsulorhexis forceps jaws.

15. The instrument handle of claim 13 wherein a decompression of the actuation structure is configured to open the capsulorhexis forceps jaws.

16. The instrument handle of claim 1 wherein the tube proximal end forms a first hermetic seal with the proximal barb fitting and the tube distal end forms a second hermetic seal with the distal barb fitting.

17. The instrument handle of claim 1 wherein the tube is configured to be used in the surgical procedure and then sterilized in the medical autoclave at least three times.

18. The instrument handle of claim 1 wherein the handle base, the end plug, and the nosecone are configured to be used in the surgical procedure and then sterilized in the medical autoclave at least three times.

* * * * *